US 8,465,550 B2

(12) United States Patent
Cartillier et al.

(10) Patent No.: US 8,465,550 B2
(45) Date of Patent: Jun. 18, 2013

(54) LINE OF COTYLOID IMPLANTS OF DIFFERENT SIZES

(76) Inventors: Jean Claude Cartillier, Lyons (FR); Alain Machenaud, La Balme De Sillingy (FR); Tarik Ait Si Selmi, Lyons (FR); Jean-Charles Rollier, Saint Martin Bellevue (FR); Michel Bonnin, Lyons (FR); Laurent Jacquoit, Charvonnex (FR); Bruno Balay, Trevoux (FR); Claude Charlet, Saint Dider Au Mont D'Or (FR); Michel Henri Fessy, Saint Genis Laval (FR); Jean Marc Semay, St. Preist en Jarez (FR); Louis Setiey, Gleize (FR); Jean-Christophe Chatelet, Jassans (FR); Jean Pierre Vidalain, Annency le Vieux (FR)

( * ) Notice: Subject to any disclaimer, the term of this patent is extended or adjusted under 35 U.S.C. 154(b) by 24 days.

(21) Appl. No.: 13/080,992

(22) Filed: Apr. 6, 2011

(65) Prior Publication Data
US 2011/0251696 A1    Oct. 13, 2011

(30) Foreign Application Priority Data
Apr. 8, 2010   (FR) .................. 10 52639

(51) Int. Cl.
*A61F 2/32*     (2006.01)
*A61F 2/34*     (2006.01)

(52) U.S. Cl.
USPC ............. 623/22.24; 623/22.21; 623/22.43

(58) Field of Classification Search
USPC .................. 623/22.21, 22.24, 23.43
See application file for complete search history.

(56) References Cited

U.S. PATENT DOCUMENTS

| | | | | |
|---|---|---|---|---|
| 4,666,448 A | * | 5/1987 | Ganz | 623/22.23 |
| 4,704,127 A | * | 11/1987 | Averill et al. | 623/22.23 |
| 5,782,928 A | * | 7/1998 | Ries et al. | 623/22.21 |
| 5,879,401 A | * | 3/1999 | Besemer et al. | 623/22.28 |
| 2006/0004463 A1 | * | 1/2006 | Lewis et al. | 623/22.38 |
| 2006/0217815 A1 | * | 9/2006 | Gibbs et al. | 623/22.17 |

* cited by examiner

*Primary Examiner* — Bruce E Snow
*Assistant Examiner* — Melissa Hoban
(74) *Attorney, Agent, or Firm* — Cantor Colburn LLP

(57) ABSTRACT

A line of cotyloid implants of different sizes including a cup intended to be fastened in a cotyloid cavity and including a substantially hemispherical polar portion and an equatorial portion extending the polar portion, the polar portion and the equatorial portion delimiting a substantially hemispherical inner cavity, an insert pivotally mounted in the inner cavity delimited by the polar and equatorial portions of the cup, the insert delimiting an inner cavity having an inner spherical surface portion and intended to pivotally and retentively mount a prosthetic femoral head, where the height of the equatorial portions of the cups of the various cotyloid implants belonging to the line varies in a decreasing manner as a function of the increase in the size of the cotyloid implants.

11 Claims, 2 Drawing Sheets

LINE OF COTYLOID IMPLANTS OF DIFFERENT SIZES

TECHNICAL FIELD

The present invention relates to a line of cotyloid implants, and more particularly a line of so-called "dual mobility" cotyloid implants.

BACKGROUND

A dual mobility cotyloid implant includes, in a known manner, on one hand a cup intended to be fastened in a cotyloid cavity and including a substantially hemispherical polar portion and an equatorial portion extending the polar portion, said polar portion and the equatorial portion delimiting a substantially hemispherical inner cavity, and on the other hand an insert pivotally mounted in the inner cavity delimited by the polar and equatorial portions of the cup, the insert being outwardly delimited by an outer spherical surface portion and itself delimiting an inner cavity having an inner spherical surface portion and intended to pivotally and retentively assemble a prosthetic femoral head.

The present of such an equatorial portion makes it possible to limit the risks of an insert leaving the corresponding cup, and therefore the risks of luxation of the implant. Such a cotyloid implant therefore limits repeated surgeries.

It must, however, be noted that the risks of luxation remain significant when the "jumping distance," i.e. the distance separating the bottom of the cup and the edge delimiting the opening thereof, is small, which is normally the case for the small implant sizes.

In order to limit the risks of luxation for small implant sizes, it is known to provide a substantial and constant equatorial portion height for all of the implants belonging to a line so as to ensure a satisfactory jumping distance for all of the implants.

However, the equatorial portion of the cup of such a cotyloid implant may, for large implants, come into conflict with the muscles or tendons situated close to the acetabular bone, and in particular with the patient's psoas, and therefore cause pain for the patient.

In order to reduce the risks of luxation, it is also known to offset the centers of the outer and inner spherical surface portions of the insert so that the center of the inner spherical surface portion is situated on the bottom side of the inner cavity delimited by the insert. These arrangements make it possible to ensure optimal repositioning of the insert relative to the cup in the upright position of the patient, due to the torque created by the forces exerted on the prosthetic femoral head, which causes the insert to rotate until it is in the balanced position.

It must, however, be noted that the offset between these two centers may not be sufficient to ensure optimal repositioning of the insert for large implants. Indeed, the larger the implant, the more the friction between the outer surface of the insert and the inner surface of the cup are significant and thereby oppose the torque created by the forces exerted on the prosthetic femoral head and aiming to replace the insert, which can cause a risk of luxation of the femoral prosthetic head and thus damage the reliability of the implant.

BRIEF SUMMARY

The present invention aims to resolve these drawbacks.
The invention provides a line of cotyloid implants that have a simple structure and are economical and reliable, while also making it possible to avoid the risks of luxation and conflict with the patient's body.

To that end, the invention relates to a line of cotyloid implants of different sizes of the type comprising:
- a cup intended to be fastened in a cotyloid cavity and including a substantially hemispherical polar portion and an equatorial portion extending the polar portion, the polar portion and the equatorial portion delimiting a substantially hemispherical inner cavity.
- an insert pivotally mounted in the inner cavity delimited by the polar and equatorial portions of the cup, the insert delimiting an inner cavity having an inner spherical surface portion and intended to pivotally and retentively mount a prosthetic femoral head, characterized in that the height of the equatorial portions of the cups of the various cotyloid implants belonging to the line varies in a decreasing manner as a function of the increase in the size of the cotyloid implants.

Thus, the height of the equatorial part of the cup of the smallest implant can be defined as significant in order to promote the stability of the small implants, without this being detrimental for the large implants. Indeed, due to the decrease in the height of the equatorial portions as a function of the increase in the size of the cotyloid implants, the height of the equatorial portions of the cups of the large implants is small such that the cups thereof are not likely to create conflicts with the patient's body, and in particular the patient's psoas. As a result, the line according to the invention makes it possible to avoid the risks of luxation, while also avoiding the risks of conflicts with the patient's body.

Preferably, the height of the equatorial portions of the cups of the various cotyloid implants belonging to the line decreases homothetically or by levels between two successive sizes of cotyloid implants.

According to one embodiment, the equatorial portion of each cup extends over the entire periphery thereof.

Advantageously, each insert is outwardly delimited by an outer spherical surface portion, and the center of the inner spherical surface portion of the insert of at least one of the cotyloid implants is offset relative to the center of the outer spherical surface portion of said insert, towards the bottom of the inner cavity delimited by said insert. Preferably, the centers of the outer and inner spherical surface portions of the insert of at least one of the cotyloid implants are offset along the axis of symmetry of the insert.

Advantageously, the distance between the center of the outer spherical surface portion of the insert of a cotyloid implant and the center of the inner spherical portion of said insert varies in a manner increasing as a function of the increase in the size of the cotyloid implants. These arrangements make it possible to ensure optimal repositioning of the insert relative to the cup for all of the implants belonging to the line, and more particularly for large implants.

The distance between the center of the outer spherical surface portion of the insert of a cotyloid implant and the center of the inner spherical surface portion of said insert increases, for example homothetically or by levels between two successive sizes of cotyloid implants.

According to one embodiment, each cup has a smooth and polished inner surface.

Advantageously, the inner cavity of each insert has a spherical surface portion extending over more than a half-sphere and extended towards the opening of the insert by a forked tapered portion.

Preferably, each cup comprises, on its outer surface, bone anchoring means. The bone anchoring means advantageously include a thread extending over at least a portion of the outer surface of the polar portion, and preferably also over at least one portion of the outer surface of the equatorial portion.

It should be noted that the cotyloid implants belonging to the line can use cemented fastening or biological fastening.

Preferably, each insert is made from polyethylene, and each cup is metal, preferably stainless steel or a chrome-cobalt alloy.

Advantageously, the outer surface of each cup is rough and preferably at least one portion of the outer surface of the cup is covered with a titanium coating.

Preferably, the equatorial portion of each cup is inwardly delimited by a forked tapered surface towards the opening of said cup. These arrangements make it possible to facilitate the reinsertion of the insert into the cup in case of luxation of the latter, and therefore prevent a repeat surgical operation. Moreover, these arrangements make it possible to increase the amplitude of movement of the prosthetic femoral neck, while also reducing the risks of conflict between the latter and the cup.

BRIEF DESCRIPTION OF THE DRAWINGS

In any event, the invention will be well understood using the following description in reference to the appended diagrammatic drawing showing, as a non-limiting example, one embodiment of this line of cotyloid implants.

DETAILED DESCRIPTION

The line of cotyloid implants according to the invention can for example include six cotyloid implants of different sizes, i.e. different diameters. The cotyloid implants belonging to the line can use cemented fastening or biological fastening.

Figure 1:
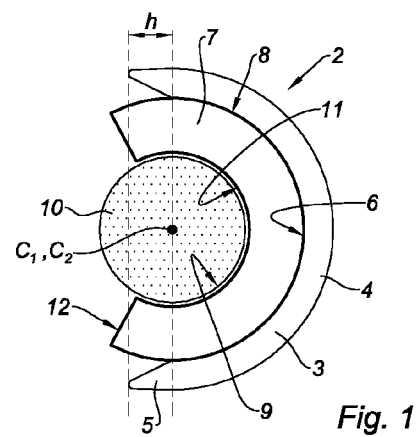
FIG. 1 is a diagrammatic cross-sectional view of the smallest cotyloid implant belonging to the line according to the invention.

As shown in FIG. 1, each cotyloid implant 2 comprises a metal cup 3 intended to be fastened in a cotyloid cavity of a patient and including a hemispherical polar portion 4 and an equatorial portion 5 extending the polar portion 4. The polar portion 4 and the equatorial portion 5 delimit a substantially hemispherical inner cavity 6. The equatorial portion 5 extends over the entire periphery of the cup and delimits the opening thereof. The equatorial portion 5 is advantageously inwardly delimited by a forked tapered surface extending from the polar portion to the opening of the cup. The equatorial portion 5 is advantageously outwardly delimited by a cylindrical surface.

Preferably, each cup 3 comprises, on its outer surface, bone anchoring means (not shown in the figures). The bone anchoring means can for example include a thread arranged on the outer surface of the equatorial portion 5.

Each cup 3 is preferably made from stainless steel or a chrome-cobalt alloy. Each cup 3 advantageously has a smooth and polished inner surface and a rough outer surface. Preferably, at least one portion of the outer surface of each cup 3 is covered with a titanium coating.

Each cotyloid implant 2 also comprises an insert 7 made from polyethylene pivotally mounted in the inner cavity 6 delimited by the polar and equatorial portions 4, 5 of the cup. Each insert 7 is outwardly delimited by an outer spherical surface portion 8 and itself delimits an inner cavity 9 intended to pivotally and retentively mount a prosthetic femoral head 10. The inner cavity 9 of each insert has an inner spherical surface portion 11 extending over more than a half-sphere and extended towards the opening of the insert by a forked tapered portion 12.

As shown in FIG. 1, the center $C_1$ of the outer spherical surface portion 8 of the insert of the smallest cotyloid implant 2 is combined with the center $C_2$ of the inner spherical surface portion 11 of said insert.

Figure 2:
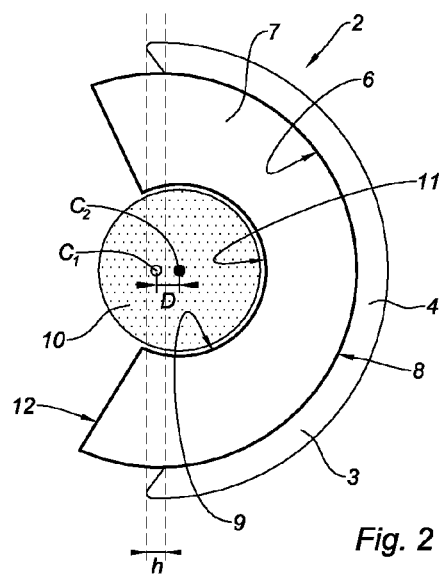
FIG. 2 is a diagrammatic cross-sectional view of the largest cotyloid implant belonging to the line according to the invention.

As shown in FIG. 2, the center $C_2$ of the inner spherical surface portion 11 of the insert of the largest cotyloid implant 2 is offset by a distance D relative to the center $C_1$ of the outer spherical surface portion 8 of said insert, along the axis of symmetry of the insert and towards the bottom of the inner cavity 9 delimited by said insert.

The height h of the equatorial portions 5 of the cups 3 of the various cotyloid implants 2 belonging to the line varies in a decreasing manner as a function of the increase in the size of the cotyloid implants. Preferably, the height of the equatorial portions 5 of the cups 3 of the various cotyloid implants belonging to the line decreases homothetically or by levels between two successive sizes of cotyloid implants. It should be noted that the height h is maximal for the smallest cotyloid implant and minimal for the largest cotyloid implant.

Advantageously, the distance D between the center $C_1$ of the outer spherical surface portion 8 of the insert of a cotyloid implant and the center $C_2$ of the inner spherical surface portion 11 of said insert varies in an increasing manner as a function of the increase in the size of the cotyloid implants. The distance D between the center $C_1$ of the outer spherical surface portion 8 of the insert of a cotyloid implant and the center $C_2$ of the inner spherical surface portion 11 of said insert increases for example homothetically or by levels between two successive sizes of cotyloid implants. It should be noted that the distance D is null for the smallest cotyloid implant and maximal for the largest cotyloid implant.

Figure 3:
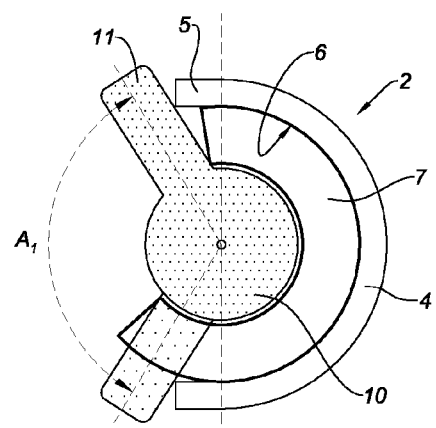
FIG. 3 is a diagrammatic cross-sectional view of the smallest cotyloid implant according to one alternative embodiment of the invention.

FIG. 3 shows a cotyloid implant 2 that differs from that shown in FIG. 1 essentially in that the equatorial portion 5 is cylindrical. The amplitude of movement $A_1$ of a prosthetic femoral neck 11 inside the cotyloid implant 2 is shown in FIG. 3 by illustrating the two extreme positions of the prosthetic femoral neck 11.

Figure 4:
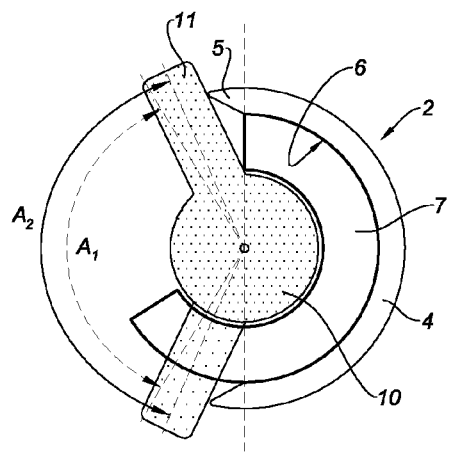
FIG. 4 is a diagrammatic cross-sectional view of the cotyloid implant of FIG. 1 showing the amplitude of movement of a prosthetic femoral neck in the implant of FIG. 1 and in the implant of FIG. 3, respectively.

FIG. 4 illustrates the amplitudes of movement $A_1$ and $A_2$ of a prosthetic femoral neck 11 respectively inside the cotyloid implant of FIG. 3 and inside the cotyloid implant of FIG. 1. As shown in FIG. 4, inwardly delimiting the equatorial portion 5 of each cup by a forked tapered surface towards the opening of said cup makes it possible to increase the amplitude of movement of the prosthetic femoral neck 11 inside the cotyloid implant.

As goes without saying, the invention is not limited solely to the embodiment of this line of cotyloid implants described above as an example, but on the contrary encompasses all alternative embodiments.

The invention claimed is:

1. A line of cotyloid implants of different sizes, comprising:
    a cup intended to be fastened in a cotyloid cavity and including a hemispherical polar portion and an equatorial portion extending the polar portion, the polar portion and the equatorial portion delimiting a substantially hemispherical inner cavity, an insert pivotally mounted in the inner cavity delimited by the polar and equatorial portions of the cup, the insert delimiting an inner cavity having an inner spherical surface portion and intended to pivotally and retentively mount a prosthetic femoral head, wherein the equatorial portion extends from a circumferential edge of the hemispherical polar portion, and a height of the equatorial portions of each of the cups of the various cotyloid implants belonging to the line varies in a decreasing manner as a function of an increase in a size of the cotyloid implants.

2. The line according to claim 1, wherein the height of the equatorial portions of the cups of the various cotyloid implants belonging to the line decreases homothetically or by levels between two successive sizes of cotyloid implants.

3. The line according to claim 1, wherein each insert is outwardly delimited by an outer spherical surface portion, and a center of the inner spherical surface portion of the insert of at least one of the cotyloid implants is offset relative to a center of the outer spherical surface portion of said insert, towards a bottom of the inner cavity delimited by said insert.

4. The line according to claim 3, wherein the centers of the outer and inner spherical surface portions of the insert of at least one of the cotyloid implants are offset along an axis of symmetry of the insert.

5. The line according to claim 3, wherein a distance between the center of the outer spherical surface portion of the insert of a cotyloid implant and the center of the inner spherical portion of said insert varies in a manner increasing as a function of the increase in the size of the cotyloid implants.

6. The line according to claim 5, wherein the distance between the center of the outer spherical surface portion of the insert of a cotyloid implant and the center of the inner spherical surface portion of said insert increases homothetically or by levels between two successive sizes of cotyloid implants.

7. The line according to claim 1, wherein each cup has a smooth and polished inner surface.

8. The line according to claim 1, wherein the inner cavity of each insert has a spherical surface portion extending over more than a half-sphere and extended towards an opening of the insert by a forked tapered portion.

9. The line according to claim 1, wherein each cup comprises, on its outer surface, bone anchoring means.

10. The line according to claim 1, wherein the equatorial portion of each cup is inwardly delimited by a forked tapered surface towards an opening of said cup.

11. The line according to claim 1, wherein the equatorial portion extends substantially perpendicularly to an equatorial plane defined by the circumferential edge of the hemispherical polar portion.

* * * * *